United States Patent
Decker et al.

(10) Patent No.: US 10,022,470 B2
(45) Date of Patent: Jul. 17, 2018

(54) HIGH-STRENGTH AND BIO-ABSORBABLE MAGNESIUM ALLOYS

(71) Applicant: THIXOMAT, INC., Livonia, MI (US)

(72) Inventors: Raymond Decker, Ann Arbor, MI (US); Stephen LeBeau, Northville, MI (US); Steven Young, Redford, MI (US)

(73) Assignee: THIXOMAT, INC., Livonia, MI (US)

( * ) Notice: Subject to any disclaimer, the term of this patent is extended or adjusted under 35 U.S.C. 154(b) by 211 days.

(21) Appl. No.: 14/777,159

(22) PCT Filed: Mar. 17, 2014

(86) PCT No.: PCT/US2014/030477
§ 371 (c)(1),
(2) Date: Sep. 15, 2015

(87) PCT Pub. No.: WO2014/145672
PCT Pub. Date: Sep. 18, 2014

(65) Prior Publication Data
US 2016/0022863 A1 Jan. 28, 2016

Related U.S. Application Data

(60) Provisional application No. 61/788,384, filed on Mar. 15, 2013.

(51) Int. Cl.
| | |
|---|---|
| *A61L 27/04* | (2006.01) |
| *C22F 1/06* | (2006.01) |
| *C22C 23/04* | (2006.01) |
| *C22F 1/00* | (2006.01) |
| *A61L 31/02* | (2006.01) |

(Continued)

(52) U.S. Cl.
CPC .......... *A61L 27/047* (2013.01); *A61L 31/022* (2013.01); *A61L 31/148* (2013.01); *C22C 23/04* (2013.01); *C22F 1/002* (2013.01); *C22F 1/06* (2013.01); *A61B 17/064* (2013.01);
(Continued)

(58) Field of Classification Search
CPC .......... A61L 27/04; A61L 27/047; C22F 1/06; C22F 1/002; C22C 23/04
See application file for complete search history.

(56) References Cited

U.S. PATENT DOCUMENTS

| | | | |
|---|---|---|---|
| 2009/0131540 A1 | 5/2009 | Hiromoto et al. | |
| 2009/0196787 A1* | 8/2009 | Beals ................. | C22C 23/02 420/409 |

(Continued)

FOREIGN PATENT DOCUMENTS

| | | |
|---|---|---|
| CN | 101392344 A | 3/2009 |
| CN | 101629260 A | 1/2010 |

OTHER PUBLICATIONS

International Search Report of PCT/US2014/030477 dated Aug. 6, 2014 by the Korean Intellectual Property Office as International Search Authority.

*Primary Examiner* — Christopher Beccia
(74) *Attorney, Agent, or Firm* — Eric J. Sosenko; Jonathan P. O'Brien; Honigman Miller Schwartz and Cohn LLP

(57) ABSTRACT

A microalloyed magnesium material for absorption in the body of a human or animal. The microalloyed magnesium material consists of: 0.85 to 1.4 percent by weight of zinc (Zn), 0.2 to 0.5 percent by weight of calcium (Ca), 0.2 to 0.5 percent by weight of manganese (Mn) with the remainder being magnesium (Mg) and inevitable impurities.

27 Claims, 6 Drawing Sheets

$H_2$ evolution in corrosion of experimental alloys in SBF at 37°C

(51) Int. Cl.
 *A61L 31/14* (2006.01)
 *A61B 17/064* (2006.01)
 *A61B 17/00* (2006.01)
 *A61B 17/84* (2006.01)

(52) U.S. Cl.
 CPC ........... *A61B 17/0642* (2013.01); *A61B 17/84* (2013.01); *A61B 2017/00004* (2013.01); *A61L 2430/02* (2013.01)

(56) References Cited

U.S. PATENT DOCUMENTS

| | | | |
|---|---|---|---|
| 2011/0172724 A1* | 7/2011 | Hort | A61L 24/0063 606/86 R |
| 2012/0269673 A1 | 10/2012 | Koo et al. | |
| 2012/0305145 A1 | 12/2012 | Decker et al. | |
| 2013/0144290 A1* | 6/2013 | Schiffl | C22C 23/04 606/62 |
| 2013/0218265 A1* | 8/2013 | Becher | A61F 2/06 623/1.46 |
| 2014/0236284 A1* | 8/2014 | Stinson | A61L 31/022 623/1.38 |

* cited by examiner

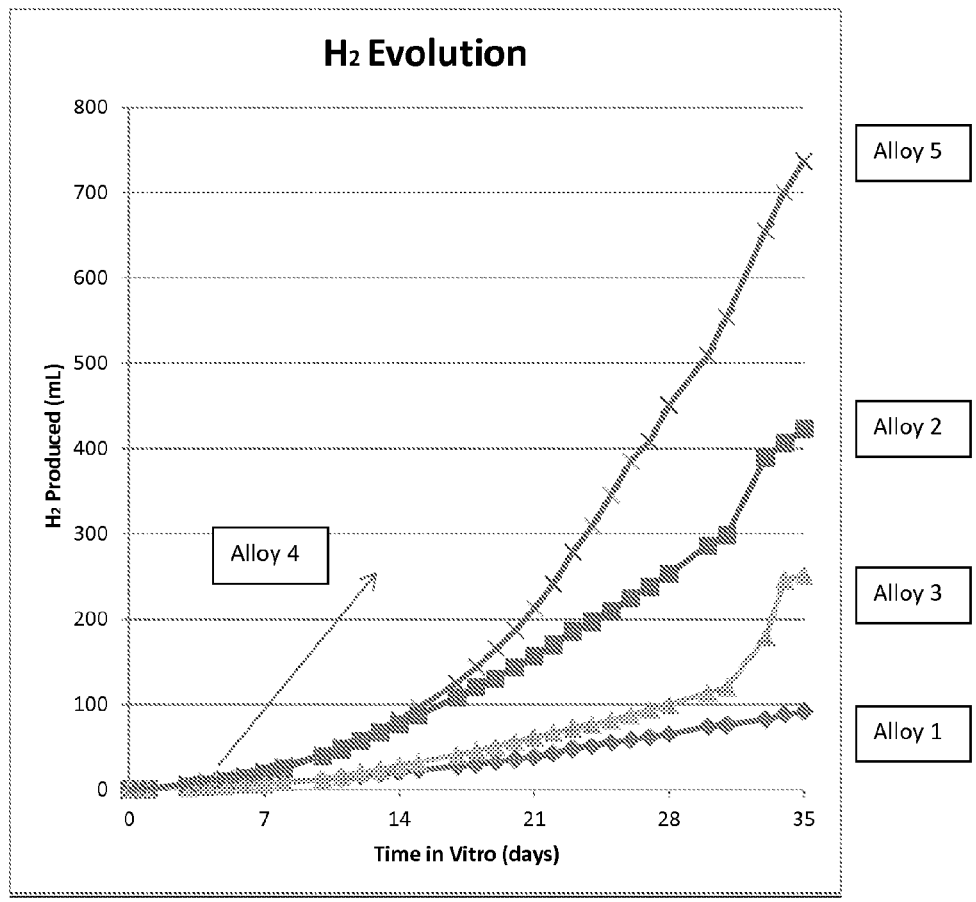
FIG. 1 - H₂ evolution in corrosion of experimental alloys in SBF at 37°C

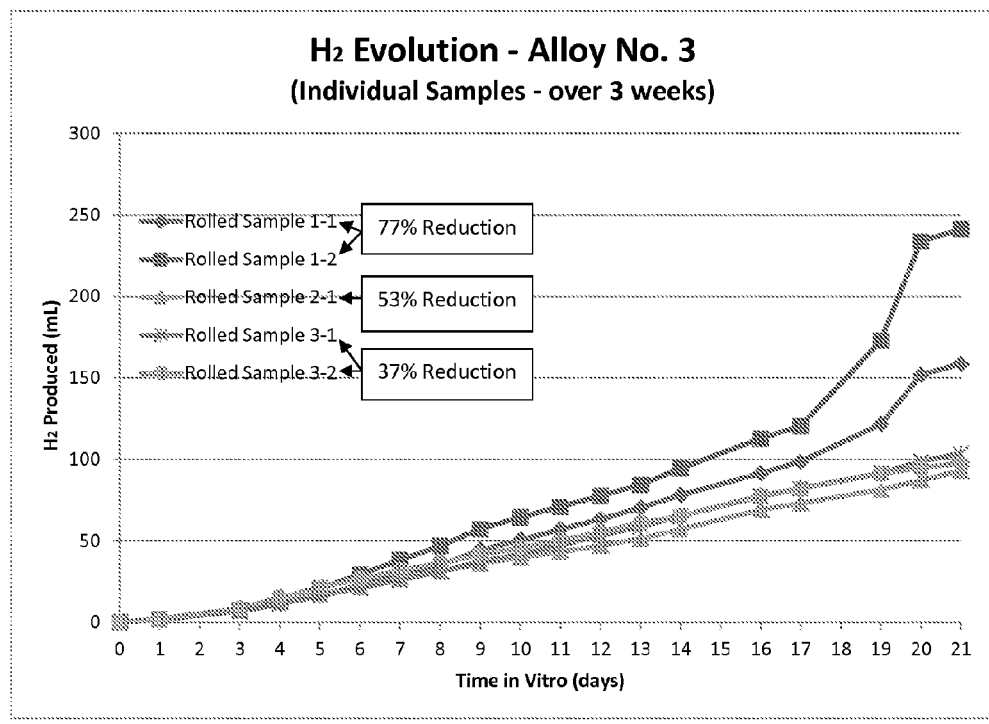
FIG. 2 - Effect of % rolling reduction on $H_2$ release from Alloy No. 3 in SBF at 37°C

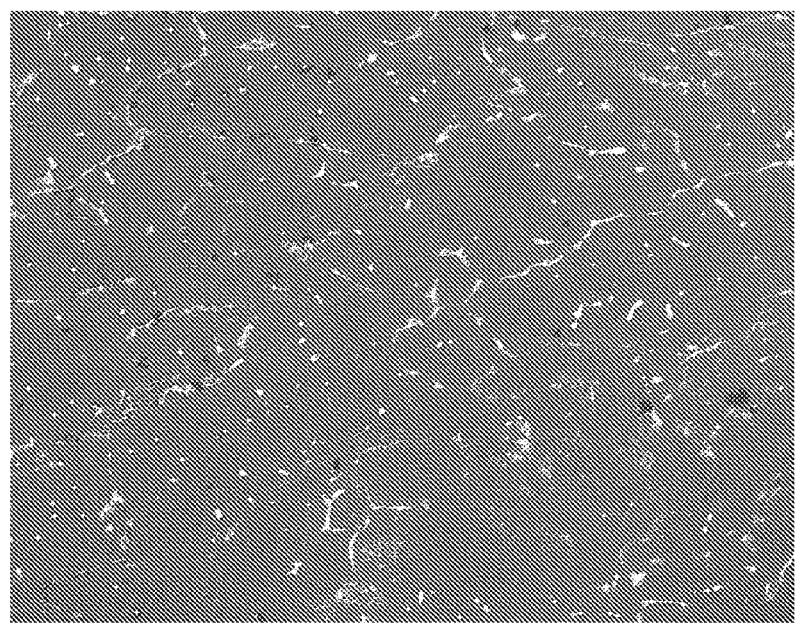
Figure 3 - Electron micrograph of Alloy No. 7, Mg-4.1Zn-0.34Ca-0.62Mn, showing coarse grain boundary Mg/Ca-Zn intermetallic phases
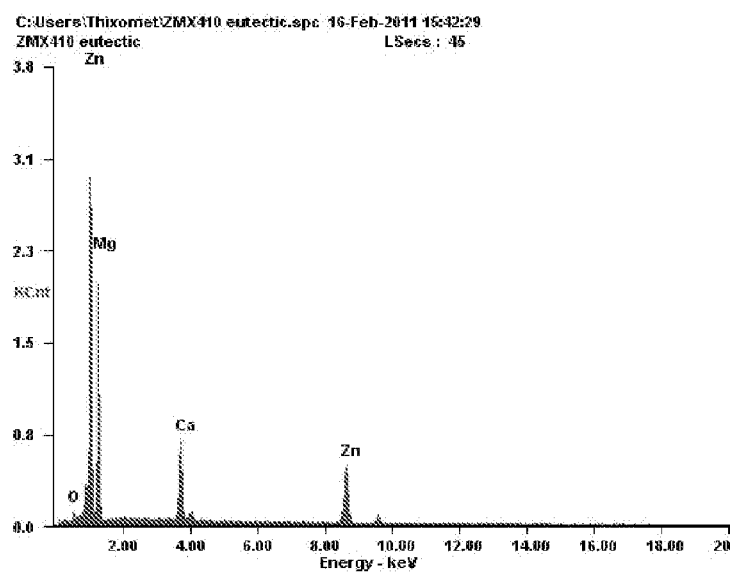
FIG. 4 - Electron diffraction pattern from grain boundary phases in Figure 3, showing high Ca and Zn content.

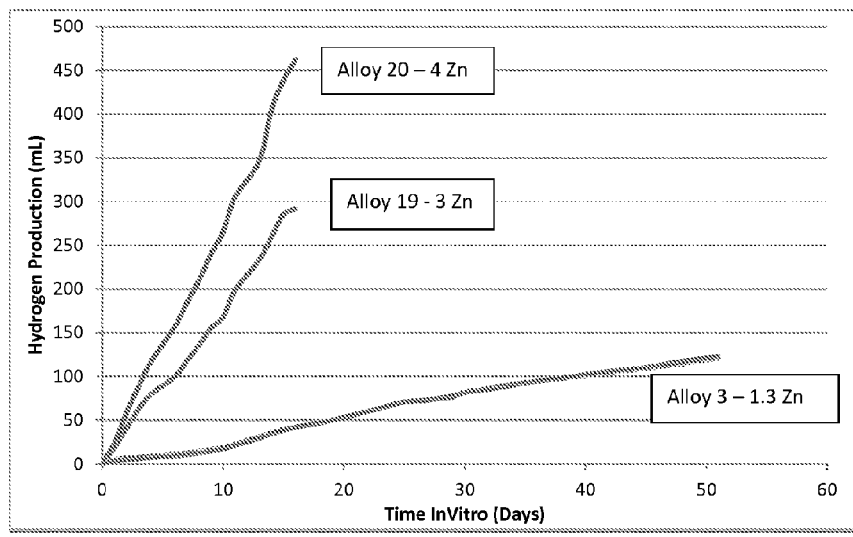
FIG. 5 - Effect of Zn content on $H_2$ Evolution of Mg-Zn-Ca-Mn alloy
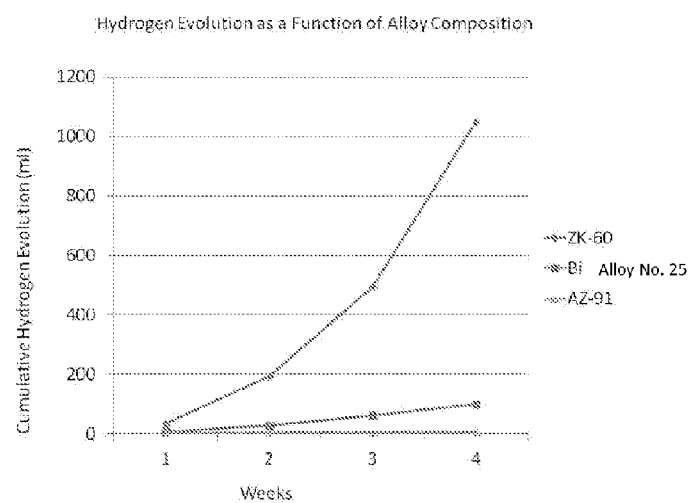
FIG. 6 - Comparison of corrosion rate of micro-alloyed Alloy No. 25 with commercially available ZK60 and AZ91D

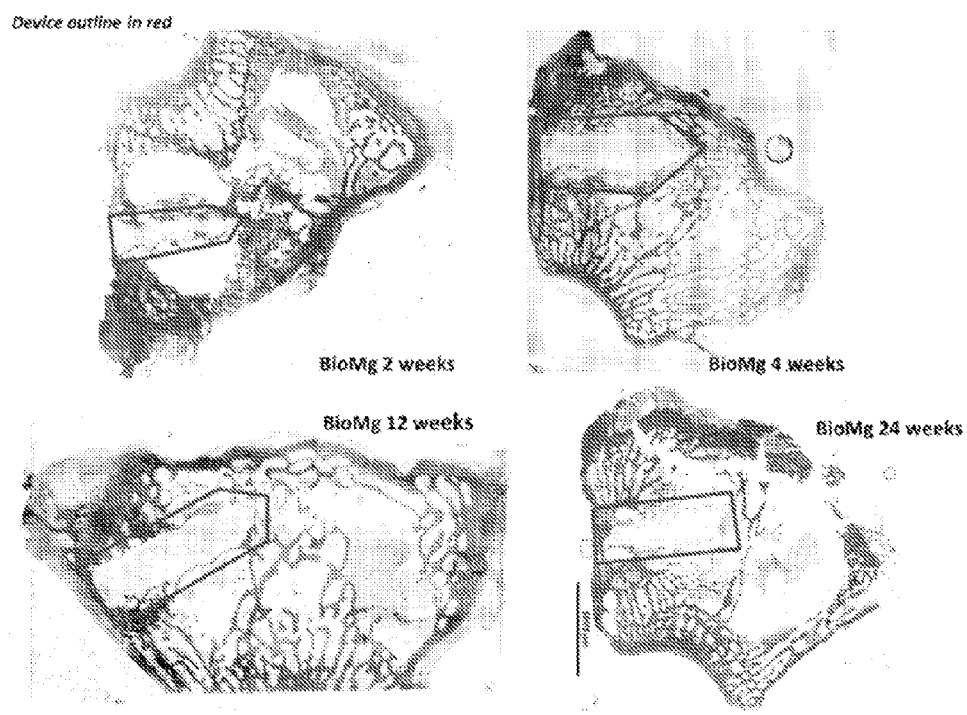
FIG 7 - Histology data for several cohort with Alloy No. 25 implant
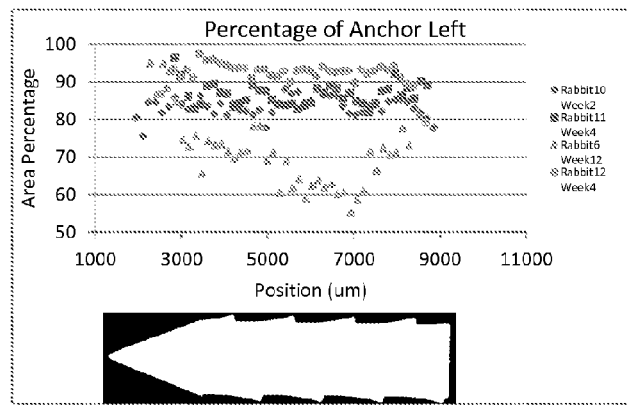
FIG. 8 - Graph of corrosion behavior as determined in 2d slice analysis several cohort samples

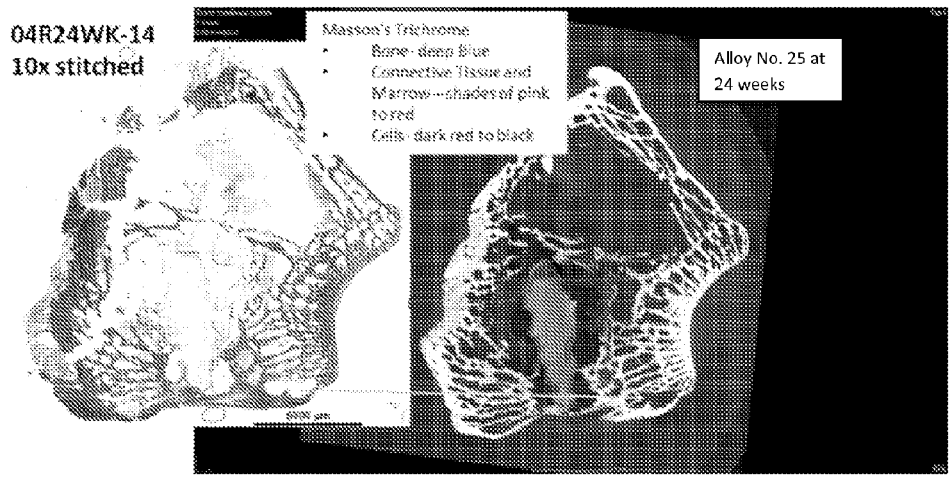
FIG. 9 - Co-localized data: histology (left) and X-ray CT (right) for week 24 explant
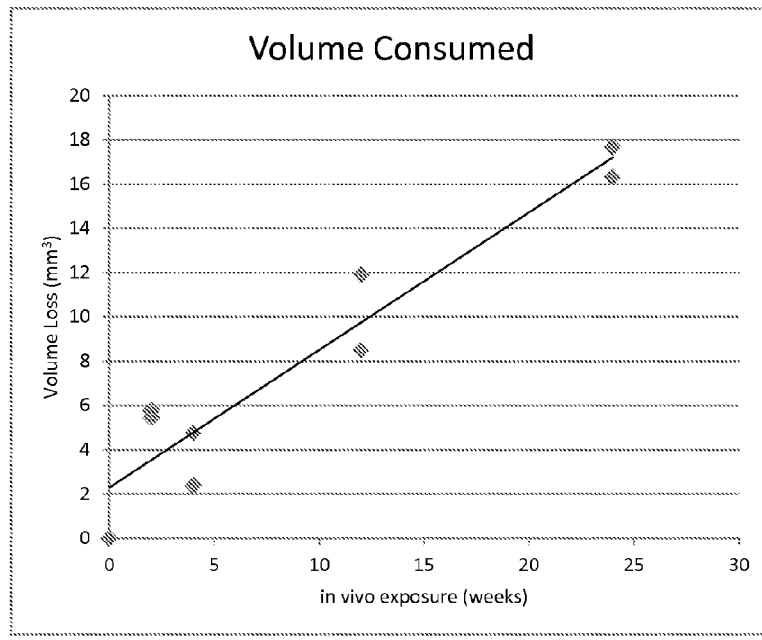
FIG. 10 - Graph of estimated volume loss (+/- 15%) vs in vivo exposure

HIGH-STRENGTH AND BIO-ABSORBABLE MAGNESIUM ALLOYS

CROSS-REFERENCE TO RELATED APPLICATIONS

This application is the U.S. national phase of PCT Application No. PCT/US2014/030477 filed on Mar. 17, 2014, which claims benefit of U.S. Provisional Patent Application No. 61/788,384 filed Mar. 15, 2013, the disclosures of which are incorporated in their entirety by reference herein.

STATEMENT OF GOVERNMENT SUPPORT

This invention was made with Government support under NSF STTR Project No. 0847198 awarded by the National Science Foundation. The U.S. Government has certain rights to this invention.

BACKGROUND

1. Field of the Invention

The present invention generally relates to surgical device. More specifically, the present invention relates to bio-absorbable surgical devices, including implantable devices for fixating bone and tissue and non-implantable surgical devices.

2. Related Technology

The overall market for orthopedic implants is large at $43 B p.a. worldwide (2012 estimate, Frost and Sullivan) with $14 B p.a. for reconstruction devices and $4 B p.a. for trauma fixation devices. In the U.S., over 2.5 million implant and ligament repair procedures are performed annually. Ligament repair procedures alone have been estimated to be greater than 700,000 p.a. In smaller countries, such as in Germany, there are over 500,000 p.a. that require fixation with surgical bone implants. Of these, 300,000 or so need rescission surgery to remove the implants, at a cost of $700 MM p.a. The cost of U.S. DOD secondary removal operations is estimated at $500 MM p.a. The health system savings in fostering faster recovery and the avoidance of infection and inflammation treatments with a new technology could be very significant.

Surgeons need more effective measures to correct ligament and bone damage, such as those which occur in shoulder lesions, anterior cruciate ligaments, hamstrings and bone fractures of various types, including craniofacial fractures. Currently, a wide variety of techniques are used in these reparative surgeries, including permanent non-absorbable implants, temporary non-absorbable implants and bio-absorbable polymer implants.

A gradual load transfer from an implant to the healing bone and tissue is desired in these reparative surgeries. Permanent metal fixation devices or implants, while strong, do not allow for the proper loading of the fixated bones to enable them to sufficiently regrow. Plastic fixation devices fall short of mimicking bone properties. Neither type of fixation device affords the gradual transfer of loading. Metal fixation devices further also interfere with post-operative magnetic resonance imaging (MRI) scanning, and in some instances, the fixation devices require subsequent surgeries for removal of the fixation device. There is lost productive time, physiological harm, threat of infection and pain that results from secondary operations to remove the fixation devices, particularly in the removal of craniofacial fixation devices and those from ligaments and small bones, such as those in the hands, toes and ankles. The needing cost associated with such removals is extensive.

Biodegradable plastics are also sometimes used as the fixation devices to allow repaired ligaments to heal and strengthen. As noted above, such plastic fixation devices do not properly mimic bone characteristics in terms of strength. Nor do these polymer implants encourage bone growth on their receding surface as they absorb. Stronger, tougher and stiffer materials in the current biodegradable plastics are needed for these procedures.

In many surgical procedures, metal instruments, such as retractors, are commonplace. During their use, it is possible that metal fragments are formed and accidentally left in the body of the patient as the surgery site is closed up. If the retractors are fabricated from a noncorrosive material, such as stainless steel and titanium, these metal fragments can be damaging to organs.

From the above, it is seen that implants and retractors, of a strong, tough, and dissolvable metal, are needed.

At the same time, non-toxicity to the human body is of paramount importance for implants. As an example of concerns, the most common alloying element for magnesium (Mg) base alloys to add strength and corrosion resistance is aluminum (Al); yet the presence Al in the Mg alloy implants raises serious concerns regarding Al's possible effects on dementia and Alzheimer's disease. Other potential Mg implants contain Rare Earth (RE) elements for strengthening; but the composition of additive RE master alloys is variable, containing a mixture of RE elements—some RE elements being non-toxic and some being toxic. Also, RE elements tend to concentrate at the dissolving implant site; not being carried away by body functions as Mg is. An alloy base and its alloying elements need to meet the following requirements of non-toxicity: minimal gas bubbling around the implant; normal hematology and serum biochemistry; good osteoconductivity and osteoinductivity; enhanced attached new bone growth of improved density and strength; good cytocompatibility; non-inflammation; good adhesion of osteoblasts; even distribution of alloying elements around the implants; and the addition of essential nutrients to the body, but not exceeding yearly safe limits.

Thus, a new alloying concept is needed to regain the strength lost by removing Al while improving toughness and optimizing corrosion rate; but not exceeding the yearly safe limits on toxicity.

SUMMARY

In view the drawbacks and limitations of the known technology discussed above, the present invention provides bio-absorbable fixation devices and retractors constructed of a magnesium alloy that meets the aforementioned requirements. The magnesium alloy and processing are specifically tuned for either the fixation device application or the retractor application. In the fixation device application, the particular magnesium alloy and process can be fine-tuned to the healing time/strength requirements of the particular surgical repair. For the retractor application, the magnesium alloy and process can be tuned to provide the desired strength, allowing for fast absorption of any metal fragments retained within the body of the patient.

With the technology of the present invention, the cost, pain, psychological stress and lost productive time associated with secondary, implant removal procedures should be obviated. Faster and more durable fixations of ligaments to bones should result, and should find particular use in shoulder, craniofacial and ACL injuries. Ankle, toe and finger fractures should be treatable with less stiffness than with permanent implants. Post-implant procedures to remedy infections and inflammation should also be obviated. In addition to the above, the problems resulting from retractor or other surgical instrument fragments would be reduced, if not eliminated. Applications could be extended to lightweight external orthopedic devices.

As such, in one aspect, the invention provides a Mg alloy that is hard and strong, providing durability for the entire healing process to any fixation device made of the Mg alloy. Magnesium (Mg) is the lightest of structural metals, at 60% of the density of Al, 38% of titanium (Ti) and 20% of stainless steel or cobalt (Co) implants. The elastic modulus and yield strength of Mg alloys are closer to bone than alloys used in other metallic implants—thus use of the proposed magnesium alloys maximizing stress transfer at interfaces. Furthermore, the fracture toughness of Mg alloys exceeds that of ceramics, hydroxyapatite, polymers and ceramic implants. It is also important to note that Mg is friendly to the body. Mg is naturally found in bone tissue and is essential to human metabolism. It is also the $4^{th}$ most abundant cation in the human body, is a co-factor for many enzymes, and stabilizes both DNA and RNA. During bioabsorption, Mg from the dissolving implant alloys is absorbed into the new attached bone. As a result, this new bone is denser and stronger than the previously fractured bone.

In one aspect, the present invention therefore provides a microalloyed magnesium material for absorption in the body of a human or animal, the microalloyed magnesium material consisting of: 0.85 to 1.4 percent by weight of zinc (Zn), 0.2 to 0.5 percent by weight of calcium (Ca), 0.2 to 0.5 percent by weight of manganese (Mn) with the remainder being magnesium (Mg) and inevitable impurities.

In another aspect of the invention, the combined percent of Zn, Ca and Mn microalloyed with Mg is in the range of 1.4 to 2.4 percent.

In a further aspect of the invention, the combined percent of Zn, Ca and Mn microalloyed with Mg is in the range of 1.5 to 2.4 percent.

In an additional aspect of the invention, the Zn content is in the range of 0.9 to 1.3 percent by weight.

In yet another aspect of the invention the Ca content is in the range of 0.2 to 0.4 percent by weight.

In still a further aspect of the invention, the Mn content is in the range of 0.2 to 0.35 percent by weight.

In an additional aspect of the invention, including nanometer-sized ordered zones (mini prisms of 1-3 atom layers) of about 10×0.5 nanometers.

In another aspect, the invention provides for a surgical device formed of a material for absorption into the body of a human or animal, the surgical device comprising: a body being formed of magnesium (Mg) microalloyed with zinc (Zn), calcium (Ca) and manganese (Mn) to form a microalloyed magnesium material, the microalloyed magnesium material consisting essentially of 0.85 to 1.4 percent by weight of zinc (Zn), 0.2 to 0.5 percent by weight of calcium (Ca), 0.2 to 0.5 percent by weight of manganese (Mn) with the remainder being magnesium (Mg).

In a further aspect of the invention, the body is one of a screw, a plate, a stent, a staple, a wire or an implant device.

In another aspect of the invention, the body is part of one of a clamp, a retractor, forceps or a non-implant device.

In an additional aspect of the invention, the combined percent of Zn, Ca and Mn microalloyed with Mg is in the range of 1.4 to 2.4 percent.

In yet a further aspect of the invention, the combined percent of Zn, Ca and Mn microalloyed with Mg is in the range of 1.5 to 2.4 percent.

In still another aspect of the invention, the Zn content is in the range of 0.9 to 1.3 percent by weight.

In an additional aspect of the invention, the Ca content is in the range of 0.2 to 0.4 percent by weight.

In a further aspect of the invention, the Mn content is in the range of 0.2 to 0.35 percent by weight.

In another aspect of the invention, the microalloyed magnesium material has a yield strength in the range of 150 to 220 MPa.

In yet another aspect of the invention, the microalloyed magnesium material has an elongation percentage in the range of 15 to 35 percent.

In still a further aspect of the invention, the microalloyed magnesium material has a hardness of 60 to 84 Hv.

In an additional aspect of the invention, the microalloyed magnesium material has a grain size of less than 5 µm.

In yet a further of the invention, instill a the microalloyed magnesium material has a $H_2$ evolution rate of 50 to 150 ml per 21 days in simulated body fluid at 37° C.

In another aspect, the present invention provides for a method of manufacturing a surgical device formed at least in part of a material for absorption into the body of a human or animal, the method comprising the steps of: providing a melt of a magnesium material consisting essentially of 0.85 to 1.4 percent by weight of zinc (Zn), 0.2 to 0.5 percent by weight of calcium (Ca), 0.2 to 0.5 percent by weight of manganese (Mn) with the remainder being magnesium (Mg), the melt forming a microalloyed magnesium material; forming a casting from the microalloyed magnesium material; deforming the casting by a thermomechanical process whereby thickness of the casting is reduced an amount greater than 30 percent to form a reduced thickness wrought product; annealing the reduced thickness wrought product to form an annealed wrought product; subjecting the annealed wrought product to at least one of quenching and hardening; and forming the wrought product into at least part of surgical device.

In a further aspect of the invention, the deforming step includes rolling of the casting.

In an additional aspect of the invention, the deforming step includes extruding of the casting.

In yet another aspect of the invention, the extruding of the casting reduces the thickness of the casting by greater than 50 percent.

In still a further aspect of the invention, annealing step includes annealing in the range of 300° C. to 400° C.

In an additional aspect of the invention, annealing step includes annealing for up to 4 hours.

In still another aspect of the invention, the quenching includes water quenching.

In yet a further aspect of the invention, hardening is performed by solid solution microalloying of Zn, Ca, and Mn with Mg.

In an additional aspect of the invention, hardening is performed by forming nanometer-sized ordered zones (mini prisms of 1-3 atom layers) of about 10×0.5 nanometers.

In another aspect of the invention, the hardening includes age hardening in the range of 175° C. to 225° C. for 10 minutes to 3 hours.

In a further aspect of the invention, the forming step forms the casting into one of a screw, a plate, a stent, a staple, a wire, and an implant device.

In an additional aspect of the invention, the forming step forms the casting into one of a clamp, a retractor, forceps or a non-implant device.

In yet another aspect of the invention, the combined percent of Zn, Ca and Mn in the microalloyed magnesium material in the range of 1.4 to 2.4 percent.

In still a further aspect of the invention, the combined percent of Zn, Ca and Mn in the microalloyed magnesium material is in the range of 1.5 to 2.4 percent.

In another aspect, the present invention provides a method of fixating bone or tissue of a patient comprising the steps of: implanting a fixation device in a patient's body whereby the fixation device secures bone or tissue of the patient together, the fixation device being formed of magnesium (Mg) microalloyed with zinc (Zn), calcium (Ca) and manganese (Mn) to form a microalloyed magnesium material, the microalloyed magnesium material consisting essentially of 0.85 to 1.4 percent by weight of zinc (Zn), 0.2 to 0.5 percent by weight of calcium (Ca), 0.2 to 0.5 percent by weight of manganese (Mn) with the remainder being magnesium (Mg); absorbing the fixation device in the patient's body over time as the bone or tissue heals; and continuing to absorb the fixation device in the patient's body over time until the fixation device has been completely absorbed into the body of the patient, whereby surgical removal of the fixation device is not performed on the patient.

In a further aspect of the invention, the absorbing of the fixation device in the patient's body over time corresponds to a healing time for the bone or tissue secured by the fixation device.

In an additional aspect of the invention, the combined percent of Zn, Ca and Mn in the microalloyed magnesium material is varied in the range of 1.5 to 2.4 percent to correspond the absorbing of the fixation device in the patient's body over time to a healing time for the bone and tissue secured by the fixation device.

In still another aspect of the invention, the fixation device is one of a screw, plate, sheet, wire or stent.

BRIEF DESCRIPTION OF THE DRAWINGS

FIG. 1 is a graph presenting the evolution of various alloys in simulated body fluid;

FIG. 2 a graph presenting the effects of rolling reduction on the evolution of $H_2$ from one of the alloys presented in FIG. 1;

FIG. 3 is an electron micrograph of an alloy showing a coarse grain boundary therein;

FIG. 4 is an electron diffraction pattern of the alloy seen in FIG. 3;

FIG. 5 is a graph presenting the effects of zinc content on the evolution of $H_2$ from various alloys;

FIG. 6 is a graph corrosion rates of one alloy with respect to two commercially available alloys;

FIG. 7 is a presentation of histology data of an implant form from an alloy in accordance with the principles of the present invention;

FIG. 8 is a graph presenting corrosion data for the implant after various weeks of implantation;

FIG. 9 shows both the histology and x-ray CT images for an implant after 24 weeks; and FIG. 10 is a graph presenting the volume loss of an implant as a function of in vivo exposure over a course of weeks.

DETAILED DESCRIPTION

Mg has a tendency to corrode in the body. This corrosion is an advantage with the present invention. When the Mg alloy is used in the formation of implants, the implants become temporary and do not require a secondary operation for their removal. Rather, the Mg alloy, and therefore the implants, will be absorbed by the body. This corrosion can further be beneficially utilized to provide an intra-body, electrochemical mechanism for the delivery of medicaments. Infections and inflammation will be further reduced as a result of the reduction in secondary surgeries In accordance with the present invention, alloying elements, as replacements for Al and RE, were selected to strengthen and toughen the Mg base, while serving as nutrients and having tuned corrosion rates. The concept of microalloying with small ternary alloying additions—in preference to larger singular or binary additions—was pursued to a) amplify the strengthening mechanism, b) not threaten the toxicity tolerance of the body for individual alloying elements, c) avoid excess phases that damage ductility and toughness, and d) avoid the excessive corrosion rates that are generated with excessive alloying additions. One microalloying criterion was the selection of small ternary additions all of which are strong solid solution hardeners at low levels. Such is the case with zinc (Zn), calcium (Ca) and manganese (Mn), as seen in Table I.

TABLE I

Solid Solution Hardening Potency for Elements Added To Mg

| Alloying Element | Solid Solution Potency, MPa |
|---|---|
| Zn | 33 |
| Ca | 84 |
| Mn | 121 |

Furthermore, by microalloying with multiple elements, nanometer-sized zones (mini prisms of 1-3 atom layers) of about 10×0.5 nanometers (nm) can be generated from a Mg—Zn—Ca—Mn solid solution by thermomechanical processing (TMP) and/or heat treatment. These ordered zones contain enriched contents of Zn, Ca and Mn in an ordered atomic array in the hcp Mg matrix. These elements report to the ordered zones in order to reduce misfits resulting from their difference in atomic size and electronegativity from the Mg atom. Thus, the energy state of the alloy is lowered and the stability state of the alloy is increased. It was discovered that enhanced results can be engineered by combining additions of a large atom (Ca) with two small atoms (Zn and Mn). The mixture of two small atoms assures short time access and supply of those species to the zone. The zones are developed by a thermal and/or isothermal aging treatments that are tailored, with regard to time and temperature, to afford the attraction of Zn, Ca and Mn atoms to crystal sites in the Mg lattice, wherein they assume this orderly array. The ternary elements are selected to maximize their synergistic attractive forces as a consequence of their oddness in atomic size and electronegativity (see Table II). For optimum strengthening in short aging times, microalloying speeds hardening and minimizes over aging or over alloying that might form excessive intermetallic $Ca_2Mg_6Zn_3$ (cathodic to the Mg matrix) and/or $Mg_2Ca$ (anodic to that matrix) or $Mg_2Zn$. If coarse $Mg_2Zn$, $Ca_2Mg_6Zn_3$ and/or $Mg_2Ca$ phases occur in the cast alloy, these phases are dispersed in a disconnected array by the subsequent homogenization, thermomechanical processing and heat treatment steps. Thus, the anodic or cathodic and hydrogen generating roles of these coarse phases are decreased; resulting in a sufficient useful life in the body to fulfill their bone support mission, before the degree of absorption of the implant renders them no longer functional as a support element. However, in the case of external devices wherein fragments may be generated and left in the surgical opening, the alloy composition and processing may be tailored to add these coarse phases to accelerate corrosion.

TABLE II

Atomic Radii and Electronegativity

| Element | Size, Atomic Radius, pm | Size Difference from Mg Matrix, % | Electro-negativity | Electro-negativity Difference from Mg Matrix, % |
|---|---|---|---|---|
| Mg Matrix | 160 | — | 1.2 | — |
| Ca | 197 | +23 | 1.0 | −17 |
| Zn | 133 | −27 | 1.7 | +42 |
| Mn | 137 | −24 | 1.6 | +33 |

The cooperative attraction of Ca, Zn and Mn atoms to the ordered zone is enhanced by an increased difference in electronegativity among the large and small atoms. Thus, Ca has an affinity to share ordered arrays with Zn because of their difference of 59 in electronegativity; likewise with Mn because of the Ca—Mn electronegativity difference of 50. With the present invention, a new concept of microalloying is the use of two small atoms (Zn and Mn) for their synergistic strengthening effect; but also to afford lower contents of each to decrease their individual threats to toxicity limits. Also this microalloying by both Zn and Mn reduces the presence of coarse $Mg_2Zn$ particles that would be detrimental to toughness and corrosion resistance. In addition, microalloying with Mn counteracts the negative effect of trace Fe content on corrosion.

The selection of the Mg base and microalloying elements is also based on their nutritional functions in humans. First, Mg, Zn, Ca and Mn are all essential trace elements in the human body. For example, Mg is involved in at least 300 enzymatic reactions in the body and is needed for neuromuscular transmission, for reactions involving ATP, for protein and nucleic acid synthesis and transmission of nerve signals. Mg is regulated in the kidney, with excess Mg excreted in urine. Ca accelerates bone growth. Zn is also recognized as a highly essential element for humans. In Zn deficiency, nearly all the physiological functions are strongly perturbed. Mn plays a primary role in activating multi-enzyme systems-hydrolases, kinases, transferases, decarboxylases and micondrial respiration. The recommended daily intake (RDI) levels are 310-420 mg/d for Mg, 1000-1300 mg/d for Ca and 8-11 mg/d for Zn.

However, staying within their toxicity tolerance range is a prime factor in adopting microalloying elements. Mn can be tolerated at 0.5% in 25 g implants that dissolve in 1 year; Zn up to 1.4% in 87 g implants and Ca at 0.5% in larger implants. Microalloying all three elements afforded synergistic strengthening without exceeding the toxicity limits.

A third strengthening mechanism embodied in the present invention is grain refinement. Some refinement is afforded by microalloying; but a major refinement is by thermomechanical processing—specifically by extrusion.

Despite the strengthening rational of these three basic methodologies mentioned above, the methodologies are far from predicting the optimum combination and range of alloying elements and the optimum process. The interplay of these three mechanisms has not been modeled or determined, in prior art or science. The science and models for corrosion and ductility are lacking. In corrosion studies of binary Mg systems, the three alloying elements have exhibited mixed results that preclude prediction of the microalloyed results. This unpredictability therefore requires experimentation to discover the specific combinations and range of these three microalloying elements and the processing steps needed to create the hardening phase and optimize the Mg/Ca—Zn phases for strength, corrosion rate and toxicity.

EXAMPLE 1

Following the concepts mentioned above and as applied to implants, several Mg based alloys (identified as alloys No. 1-6 in Table III) with non-toxic alloying additions were prepared and tested. After resistance furnace melting under Ar gas and casting in steel molds, the alloys were then homogenized for 24 hours at 400° C. to dissolve large as-cast particles of Mg/Ca—Zn phases and then hot rolled at 250° C. with a greater than 50% reduction to refine the grain structure. In this Example I, the tensile properties after soaking and rolling are also listed in Table III. Yield strength and ductility were low and erratic, believed to be due to grain boundary intermetallic phases.

TABLE III

Tensile Properties of Homogenized and Rolled Alloys No. 1-6

| Alloy No. and Composition | Yield Strength, MPa | Ultimate-Tensile Strength, MPa | Elongation, % |
|---|---|---|---|
| No. 1 Mg-1.0 Zn-0.6 Ca-0.24 Mn | 170 | 182-268 | 1-9 |
| No. 2 Mg-2.1 Zn-0.3 Ca-0.27 Mn | 68 | 223 | 1 |
| No. 3 Mg-1.3 Zn-0.3 Ca-0.27 Mn | 172-204 | 213-247 | 1-5 |
| No. 4 Mg-3.0 Zn-0.3 Ca-0.48 Mn | 53-235 | 224-263 | 0-6 |
| No. 5 Mg-2.1 Zn-0.6 Ca-0.36 Mn | 51 | 228 | 1 |
| No. 6 Mg-1.2 Zn-0.36 Ca-0.21 Mn | 123 | 123 | 1 |

EXAMPLE 2

As noted in Example 1, the yield strength and ductility of the subject alloys were low and erratic. An application of a special heat treatment was found to remedy this fault in Alloy No. 6. Post-rolling solution annealing at 400° C., followed by water quenching was found to dissolve the grain boundary Mg/Ca—Zn phases and to retain the ternary elements in solid solution in a soft condition. By then aging at 200° C., the process activated the ordering of nanostructured phases to impart high strength and elongation to the alloy (see Table IV).

TABLE IV

Effects of Certain Post Rolling Treatments on Alloy No. 6 (Mg-1.2 Zn-0.36 Ca-0.21 Mn)

| Treatment | Hardness, Hv | YS, MPa | UTS, MPa | Elong., % |
|---|---|---|---|---|
| As Rolled | 58 | 123 | 123 | 1 |
| Annealed 4 hr/400° C. | 44 | | | |
| Annealed & Aged 2 hr/200° C. | 56 | 167 | 236 | 18 |

EXAMPLE 3

The annealing plus aging treatments found beneficial in Example 2 (annealing for 4 hours at 400° C., followed by water quenching then aging for 2 Hours at 200° C.) were expanded to Alloys No. 1-5 of Example I. Not only were the strength and ductilities of the Alloys No. 2-5 typically superior to their as rolled condition, but they were also superior to the most widely used commercial Mg alloy, AZ91. The strength of these alloys was also more than double that of the known commercial bio-absorbable polymer implants. Alloy No. 1, with 0.6 Ca, did not recover good strength and ductility. These results are presented in Table V.

TABLE V

Tensile Properties of Post Rolling Alloys after Annealing (4 hours at 400° C.), Water Quenching and Aging (2 hours at 200° C.)

| Alloy No. and Composition | YS, MPa | UTS, MPa | Elong., % |
|---|---|---|---|
| No. 1 Mg-1 Zn-0.6 Ca-0.24 Mn | | 198 | 5 |
| No. 2 Mg-2 Zn-0.3 Ca-0.36 Mn | 175 | 247 | 18 |
| No. 3 Mg-1.3 Zn-0.3 Ca-0.27 Mn | 171 | 250 | 18 |
| No. 4 Mg-3 Zn-0.3 Ca-0.48 Mn | 154 | 239 | 16 |
| No. 5 Mg-2.1. Zn-0.6 Ca- 0.36 Mn | 177 | 241 | 13 |
| No. 6 Mg-1.2 Zn-0.36 Ca-0.21 Mn | 167 | 236 | 18 |
| AZ91D Mg-9 Al-1 Zn (as molded) | 140 | 220 | 6 |
| Polymer Implant | | | 80 |

EXAMPLE 4

The above alloys, after annealing and aging, were tested in vitro in phosphate buffered saline solution, Simulated Body Fluid (SBF), at 37° C. to simulate bio-absorption rate in vivo. In these tests, $H_2$ evolution is a direct measure of Mg alloy corrosion, and the results are presented in Table VI.

As graphically seen in FIG. 1, the corrosion rates and $H_2$ evolution in vitro in synthetic body fluids (SBF) were very dependent upon composition. Alloy 1 demonstrated the lowest corrosion rate, while alloy 4 had the highest. In Table VI, these results are further correlated with the target times for a fixation device/implant that needs to support bone during a healing time of eight weeks, and also needing to be completely absorbed within six months. As indicated in the table, Alloys No. 1 and 3, which have low amounts of Zn, of 1.0% and 1.3% respectively, achieve these targets. Macroalloying with 2% Zn or more was seen as being detrimental to the corrosion rate, namely it being too fast to allow for adequate bone development and healing.

TABLE VI

Projected Absorption Rates of Mg Alloys

| Alloy No. and Composition | $H_2$, ml in 5 weeks | Absorption Rate For Implants |
|---|---|---|
| No. 1 Mg-1 Zn-0.6 Ca-0.24 Mn | 90 | On Target |
| No. 2 Mg-2 Zn-0.3 Ca-0.36 Mn | 430 | Too Fast |
| No. 3 Mg-1.3 Zn-0.3 Ca-0.27 Mn | 250 | Near Target |
| No. 4 Mg-3 Zn-0.3 Ca-0.48 Mn | >>740 | Much Too Fast |
| No. 5 Mg-2.1 Zn-0.6 Ca- 0.36 Mn | 740 | Much Too Fast |
| AZ91D Mg-9 Al-1 Zn-0.3 Mn | <10 | Much Too Slow, contains Al |

EXAMPLE 5

To examine the effect of the rolling practice on the alloys, the corrosion of Alloy No. 3 was tested in SBF as a function of % reduction. As shown in FIG. 2 and presented in Table VII, lesser rolling reductions (37-53%) showed lower corrosion rates than higher rolling reductions (77%). Further to the beneficial effect on corrosion, for Alloy No. 3, the 53% rolling reduction provided the best combination of strength and ductility.

TABLE VII

Effect of % Warm Reduction on Tensile Properties and Corrosion of Alloy No. 3

| Reduction, % | YS, MPa | UTS, MPa | Elong., % | $H_2$, ml in 3 weeks |
|---|---|---|---|---|
| 37 | 149 | 226 | 8 | 100 |
| 53 | 181 | 239 | 25 | 90 |
| 77 | 174 | 238 | 30 | 200 |

Thus, it was determined that the bio-absorption rate could be engineered by manipulation of both composition and processing so as to match the targets for either implantable devices and external components or instruments.

EXAMPLE 6

Coarse Mg/Ca—Zn phases were identified in a high Zn alloy of Mg-4.1 Zn-0.34 Ca-0.62 Mn, herein referred to as Alloy No. 7, wherein the resultant coarse particles are seen at grain boundaries in the electron micrograph of FIG. 3. Their high Ca and Zn content was confirmed with electron diffraction patterning, as seen FIG. 4. These grain boundary coarse phases, which are either anodic or cathodic to the Mg alloy matrix, are believed to be the cause of the faster corrosion rates seen when Zn is increased to 2% and above.

Thus, it was further determined corrosion rates can be engineered in fixation devices/implants formed from the Mg based alloy. With specific thermomechanical processing and aging, the Mg based alloy can be engineered such that the amount and distribution of coarse anodic and cathodic intermetallic Mg/Ca—Zn phases tailor the corrosion rates to match the desired life of any imbedded object formed from the alloy, whether the object is a fixation device/implant or other device.

EXAMPLE 7

In order to determine the effect of Mn on strength and ductility, a series of ternary microalloying heats, varying the Mn content, was prepared, rolled and treated (4 hr/400° C., WQ+2 hr/200° C.) as above. In the heats, the base of the alloy was composed of Mg-1 Zn-0.45 Ca, while Mn was varied from 0.2 to 0.6%. As seen in Table VIII, increased amounts of Mn decreased the grain size while increasing the strength, hardness and ductility. Optimum strength and hardness were observed at 0.4% Mn.

TABLE VIII

Effect of Mn content on Mg-1 Zn-0.45 Ca alloy, 4 hr/400° C., WQ + 2 hr/200° C.

| Alloy No. - Mn % | Grain Size, μm | YS, MPa | UTS, MPa | Elong, % | Hardness, $H_B$ |
|---|---|---|---|---|---|
| No. 8 - 0.2% | >50 | 124 | 137 | 10 | 53 |
| No. 9 - 0.3% | 32 | 129 | 227 | 12 | 53 |
| No. 10 - 0.4% | 19 | 141 | 230 | 12 | 58 |
| No. 11 - 0.6% | 12 | 140 | 242 | 14 | 56 |

EXAMPLE 8

To further affirm the effect of Mn content, in a second series of prepared, rolled and treated (4 hr/400° C., WQ+2 hr/200° C.) alloys, the Mn content was varied from 0.1 to 0.6% in Alloys No. 12-16. As seen in Table IX, again, good strength and hardness were found at 0.4% Mn, with hardness decreasing at higher Mn level of 0.6%. Thus, Mn can be capped at 0.5% to minimize any toxicity threat, since Mn has the lowest RDI levels of the alloying elements used.

TABLE IX

Effect of Mn Content on Mg-1 Zn-0.45 Ca alloy, 4 hr/400° C., WQ + 2 hr/200° C.

| Alloy No. - Mn % | YS, MPA | UTS, MPa | Elong, % | Hardness, $H_B$ |
|---|---|---|---|---|
| No. 12 - 0.1% | 132 | 208 | 6 | 48 |
| No. 13 - 0.3% | 137 | 238 | 20 | 52 |
| No. 14 - 0.4% | 145 | 242 | 13 | 57 |
| No. 15 - 0.5% | 141 | 221 | 8 | 55 |
| No. 16 - 0.6% | 142 | 246 | 18 | 53 |

EXAMPLE 9

To further affirm the negative effect of macro-alloying with Zn, as already seen in FIG. 1, additional Alloys No. 19 & 20 were prepared with higher Zn contents (see Table X and FIG. 5) and compared to an implant alloy, Alloy No. 3. It is notable that the higher Zn contents demonstrated lower strength and/or ductility, along with accelerated corrosion, which is believed to be due to presence of coarse Mg/Ca—Zn phases. Thus, Zn is capped at 1.4%.

TABLE X

Properties of Higher Zn alloys (4 hr/400° C., WQ + 2 hr/200° C.)

| No. Alloy % | YS, MPa | UTS, MPa | Elong, % | $H_2$, in 16 days, ml |
|---|---|---|---|---|
| No. 19 Mg-3 Zn-0.25 Ca-0.48 Mn | 175 | 198 | 1 | 290 |
| No. 20 Mg-4 Zn-0.34 Ca-0.62 Mn | 147 | 241 | 10 | 465 |
| No. 3 Mg-1.3 Zn-0.3 Ca-0.27 Mn | 171 | 250 | 18 | 40 |

EXAMPLE 10

In order to determine the effect of Ca content on the strength, ductility and hardness, a series of alloys, Alloy Nos. 26, 27 and 28, were prepared and rolled as above, then subsequently treated with two differing treatments. At 0.6% Ca, excessive slag formed on the melt, but excess slag did not form at 0.2% and 0.4% Ca. As a critical test, the mechanical properties in the transverse direction to rolling are listed in Table XI. (Properties in the transverse direction to rolling are usually lower than in the longitudinal direction to rolling, the latter of which is presented in the other Tables). In both the annealed and annealed+aged condition, optimum hardness and aging response were seen at 0.4% Ca. Optimum strength and elongation were also seen at 0.4% Ca. Therefore, Ca was capped at 0.5%, with a minimum of 0.2%.

TABLE XI

Effect of Ca Content on Properties, Mg - 1.2 Zn - 0.46 Mn Base

| Alloy No. - Ca % | Annealed + Age Conditioned | YS, MPa | UTS, MPa | Elong., % | Hardness, Hv |
|---|---|---|---|---|---|
| No. 26 - 0.2% | 4 hr/400 C./WQ | | | | 58 |
| No. 26 - 0.2% | 4 hr/400 C./WQ + 2 hr 200 C. | 89 | 130 | 2 | 60 |
| No. 27 - 0.4% | 4 hr/400 C./WQ | | | | 61 |
| No. 27 - 0.4% | 4 hr/400 C./WQ + 2 hr 200 C. | 107 | 206 | 7 | 74 |
| No. 28 - 0.6% | 4 hr/400 C./WQ | | | | 54 |
| No. 28 - 0.6% | 4 hr/400 C./WQ + 2 hr 200 C. | 90 | 106 | 2 | 59 |

EXAMPLE 11

To test an alternate process to rolling, Alloy No. 21, composed of Mg-0.91 Zn-0.32 Ca-0.38 Mn was cast and extruded at 300° C. with a 20/1 reduction ratio and speed of 60 inches/minute on the exiting product. With extrusion, grain size was greatly reduced to less than 5 μm, which, as seen in Table XII, afforded increased strength and elongation over the previously rolled examples of Table V.

TABLE XII

Tensile properties of extruded Mg-0.91 Zn-0.32 Ca-0.38 Mn Alloy

| Conditioned | YS, MPa | UTS, MPa | Elong, % | Red. Area, % |
|---|---|---|---|---|
| As Extruded | 210 | 265 | 18 | 24 |
| As Extruded + 2 hr/200° C. | 208 | 263 | 22 | 29 |

EXAMPLE 12

To test the lower limits on microalloying an additional alloy, Alloy No. 22 composed of Mg-0.67 Zn-0.22 Ca-0.30 Mn (a microalloying of 1.19%, the combined amount of Zn, Ca and Mn), was extruded in the same manner as Alloy No. 21. The aging response of this extrusion is compared to that of Alloy No. 21 in Table XIII. Whereas Alloy No. 21, with Mg-0.91 Zn-0.32 Ca-0.38 Mn (microalloying of 1.61%) was responsive to aging, the lower microalloying of Alloy No. 22 did not respond to age hardening. Aging increased the hardness of Alloy No. 21 by 5 Hv, within 10 to 30 minutes being a sufficient time of aging since longer aging was not seen to increase hardness. Since the hardness of Alloy No. 22 only increased minimally with initial aging, a minimum Zn content greater than 0.67% and closer to the 0.91% Zn of Alloy 21 is needed and is set at 0.85%.

TABLE XIII

Effect of Aging at 175° C. on Hardness of Extruded Alloy Nos. 21 & 22

| Alloy No. - Microalloying % | Annealed Hardness | Aging Time & Hardness, Hv | | | |
|---|---|---|---|---|---|
| | | 10 min | 30 min | 1 hr | 3 hr |
| No. 21 - 1.61% | 61 | 66 | 66 | 65 | 66 |
| No. 22 - 1.19% | 56 | 57 | 56 | | 56 |

EXAMPLE 13

To further the definition of processing and to confirm the feasibility of production on a larger scale, Alloys No. 23 and 24 were produced at the commercial production facility of Dead Sea Magnesium Ltd., located in Israel. The alloys were melted under $SF_6$ cover gas and cast into steel molds as 8 inch diameter 45 Kg billets. The billets were then extruded at 300° C. into 1.75 and 0.75 inch round bar stock. The compositions of both alloys are listed in Table XIV and tensile properties and corrosion results of Alloy No. 23 are presented in Table XV.

TABLE XIV

Composition of Alloy Nos. 23 & 24

| Alloy No. | Zn | Ca | Mn | Fe | Si | Ni | Cu | Microalloy - Zn + Ca + Mn % |
|---|---|---|---|---|---|---|---|---|
| No. 23 | 1.33 | 0.40 | 0.46 | 0.008 | 0.01 | 0.001 | 0.001 | 2.19% |
| No. 24 | 1.33 | 0.38 | 0.45 | 0.008 | 0.01 | 0.001 | 0.001 | 2.16% |

TABLE XV

Tensile Properties and SBF Results on Alloy No. 23

| Condition | YS, MPa | UTS, MPa | Elong., % | $H_2$, in 16 Days, ml |
|---|---|---|---|---|
| As Extruded | 168 | 244 | 30 | 50 |

With a fine grain size of less than 5 μm afforded by the extrusion of Alloy No. 23, the cooling rate after annealing had a pronounced effect on hardness (Table XVI), opening the way to high strengths with simple annealing treatments. Fast cooling resulted in higher hardness. The grain boundaries of the water quenched specimen were found to be free of coarse precipitates, whereas the air cooled, Kaolite insulated and furnace cooled specimens contained coarse grain boundary precipitates. In addition, in the slowest cooled (furnace cooled) specimen, overaged precipitates were evident within the grains.

TABLE XVI

Effect of Cooling Rate After Annealing (4 hr/400° C.) on Hardness of Alloy No. 23, 10 mm extrusion

| Cooling Medium | Hardness, Hv |
|---|---|
| Water Quench | 84, 81 |
| Air Cool | 78 |
| Kaolite Insulation | 58 |
| Furnace Cooling | 51 |

EXAMPLE 14

A comparison of a Al and RE free microalloyed Alloy No. 25 of Mg-1.2 Zn-0.36 Ca-0.21 Mn, was made to two commercially available alloys, alloys ZK60 (6 Zn) and AZ91D (9 Al-1 Zn). The results of the comparison is shown in FIG. 6 and presented in Table XVII. The estimated absorption time for the plate verses that for the screw differs in that the absorption time is dependent on the exposed area of the implant, and the compared plate had a greater exposed surface area than the compared screw.

TABLE XVII

Estimated Absorption Times of Alloy No. 25, ZK60 and AZ91D

| Alloy | Time for Plate, weeks | Time for Screw, weeks |
|---|---|---|
| ZK60 | 15 | 20 |
| Alloy No. 25 | 61 | 78 |
| AZ91D | 676 | 856 |

Utilizing the above concepts of alloying, for optimum melt cleanliness, strength and ductility and implant absorption rates, the content of the investigated three elements (Zn, Ca and Mn) in structural implants have been discovered to lie in the following ranges, which are given in wt. %: microalloying of Zn+Ca+Mn in the range of greater than 1.4% and less than 2.6%; Zn in the range of 0.85-1.4%; Ca in the range of 0.2-0.5%; and Mn in the range of 0.2-0.5%

EXAMPLE 15

In Vivo Animal Study: Animal experiments were conducted on Alloy No. 25 (Mg-1.2 Zn-0.36 Ca-0.21 Mn) according to approved protocol in accordance with USDA animal welfare guidelines and the NIH assurance policy on humane care and use of laboratory animals through the NCAT Institutional Animal Care and Use Committee. Each of 12 rabbits (New Zealand White and New Zealand Red crosses), older than 6 months and typically weighing in the range of 4 kg-5 kg, underwent surgery to place sample rods in drilled holes in the femoral condyle. Specifically, Mg alloy implants constructed from Alloy No. 25 were implanted in the right knee and sterile polymer PLGA-based implants were implanted in the left knee. The PLGA-based implant was used as a control group since the goal of the animal study was to establish that the histological reaction surrounding the Mg alloy implant caused no more harm than that of commercial polymer PLGA-based implant.

Each animal was sedated with a mixture of ketamine (ketamine hydrochloride 50 mg/kg) and Rompum (Xylazine, 5 mg/kg) administered intramuscularly. The animals were then intubated and placed on isoflurane inhalation anesthesia at a concentration of 0-5% as needed. Once the animal was in the proper plane of anesthesia, surgery was performed on both knees.

After access to the knee joint was obtained using osteotomy, an 8 mm deep hole was drilled through the cartilage into the cancellous part of the lateral femur condyle. Then implants (3 mm in diameter by 5 mm in height) were inserted into the drilled holes of the knees by a press fit technique. The wounds were closed by three-layer suture. Prior to implantation, the Alloy No. 25 implants were sterilized by inclusion in a standard gamma shipment to an external sterilization facility, where sterilization was conducted in the range 25-40 kGy. The rabbits were then given Buprenorphine (0.01-0.05 mg/kg) intramuscularly, 3 to 4 times, every 12 hours to control pain. The rabbits all also received 3 prophylactic doses of the antibiotic Baytril (enrofloxacin 2.5-5 mg/kg). The rabbits were examined for lameness, swellings, suture failure and general health condition every day. Sutures were removed in 7-10 days. Before sample retrieval, the animals were euthanized by an intravenous overdose of 2 ml/4.5 kg dose of 240 mg/ml pentobarbital after sedation. Once a pneumothorax has been created, the medial condyles were dissected as a block from the knee joint and placed in neutral buffered formalin (NBF) for preservation. Animals were sacrificed at 2, 4, 12, 24, and 36 weeks (n=12) weeks after surgery.

All of the rabbits in this study recovered uneventfully. All surgical incisions healed without infection. All of the rabbits were completely ambulatory, retained full range of motion, and performed complete weight bearing movements without a limp None of the rabbits exhibited any unusual behavior such as excessive licking or chewing at the surgical sites. Breathing and heart rate remained normal. In summary there were no signs of pain or discomfort as a result of the surgeries. The surgeries also did not alter any of the rabbit's gaits or attitudes.

The condyle explants were taken from their 10% Methanolic solutions and dehydrated step-wise in isopropanol/water solutions and eventually embedded into polymer. Sectioning of bone tissue was done using a microtome. Samples were stained and analyzed. FIG. 7 presents several time points of rabbit explant histological staining data. For this stain, bone stains deep blue, connective tissue and marrow stain shades of pink to red, and cells stain dark red to black. New bone was observed growing on the Mg implant Hi-resolution x-ray computed tomography characterization were performed using Nanotom-m (GE Sensing & Inspection Technologies GmbH). 3D-images were constructed for measuring volume loss in implant and to study morphological features of the corrosion process. 2D slice stack analysis was used to compare the volume of the implant after exposure to the volume defined by the original dimensions. (See FIG. 8)

Upon generation of histology data, the 3D rendered volume was oriented using the details of the stained tissue slice so that a virtual slice of CT data could be compared almost directly with the histology. In this way, the CT imaging became more informative as shades of grey become more revealing. An example of this technique is shown in FIG. 9, below. The cancellous bone is similarly patterned in both images.

As shown, there are several areas of perceived precision that can be applied to analyze the anchor volumes. The graph presented in FIG. 10 shows a qualitative volume of magnesium screw using the 3D software tool package. Utilizing this data trend and corrosion modelling[1], a dissolution rate of ~0.9 mm/yr was determined. This is near the target rate for use of Alloy No. 25 for implanted screws.

As a person skilled in the art will readily appreciate, the above description is meant as an illustration of implementation of the principles this invention. This description is not intended to limit the scope or application of this invention in that the invention is susceptible to modification, variation and change, without departing from spirit of this invention, as defined in the following claims.

We claim:

1. A microalloyed magnesium material for absorption in the body of a human or animal, the microalloyed magnesium material consisting of: 0.85 to 1.4 percent by weight of zinc (Zn), 0.2 to 0.5 percent by weight of calcium (Ca), 0.2 to 0.5 percent by weight of manganese (Mn) with the remainder being magnesium (Mg) and inevitable impurities.

2. The microalloyed magnesium material of claim 1, wherein the combined percent of Zn, Ca and Mn microalloyed with Mg is in the range of 1.4 to 2.4 percent.

3. The microalloyed magnesium material of claim 1, wherein the Mn content is in the range of 0.2 to 0.35 percent by weight.

4. The microalloyed magnesium material of claim 1, further including nanometer-sized ordered zones (mini prisms of 1-3 atom layers) of about 10×0.5 nanometers.

5. A surgical device formed of a material for absorption into the body of a human or animal, the surgical device comprising:
a body being formed of magnesium (Mg) microalloyed with zinc (Zn), calcium (Ca) and manganese (Mn) to form a microalloyed magnesium material, the microalloyed magnesium material consisting essentially of 0.85 to 1.4 percent by weight of zinc (Zn), 0.2 to 0.5 percent by weight of calcium (Ca), 0.2 to 0.5 percent by weight of manganese (Mn) with the remainder being magnesium (Mg).

6. The surgical device of claim 5, wherein the body is one of a screw, a plate, a stent, a staple, a wire or an implant device.

7. The surgical device of claim 5, wherein the body is part of one of a clamp, a retractor, forceps or a non-implant device.

8. The surgical device of claim 5, wherein the combined percent of Zn, Ca and Mn microalloyed with Mg is in the range of 1.4 to 2.4 percent.

9. The surgical device of claim 5, wherein the Mn content is in the range of 0.2 to 0.35 percent by weight.

10. The surgical device of claim 5, wherein the microalloyed magnesium material has a yield strength in the range of 150 to 220 MPa.

11. The surgical device of claim 5, wherein the microalloyed magnesium material has an elongation percentage in the range of 15 to 35 percent.

12. The surgical device of claim 5, wherein the microalloyed magnesium material has a grain size of less than 5 μm.

13. The surgical device of claim 5, wherein the microalloyed magnesium material has a H2 evolution rate of 50 to 150 ml per 21 days in simulated body fluid at 37° C.

14. A method of manufacturing a surgical device formed at least in part of a material for absorption into the body of a human or animal, the method comprising the steps of:
providing a melt of a magnesium material consisting essentially of 0.85 to 1.4 percent by weight of zinc (Zn), 0.2 to 0.5 percent by weight of calcium (Ca), 0.2 to 0.5 percent by weight of manganese (Mn) with the remainder being magnesium (Mg), the melt forming a microalloyed magnesium material;
forming a casting from the microalloyed magnesium material;
deforming the casting resulting in thermomechanical process whereby thickness of the casting is reduced an amount greater than 30 percent to form a reduced thickness wrought product;
annealing the reduced thickness wrought product to form an annealed wrought product; subjecting the annealed wrought product to at least one of quenching and hardening; and
forming the wrought product into at least part of surgical device.

15. The method of manufacturing a surgical device according to claim 14, wherein the deforming step includes rolling of the casting.

16. The method of manufacturing a surgical device according to claim 14, wherein the deforming step includes extruding of the casting.

17. The method of manufacturing a surgical device according to claim 14, wherein annealing step includes annealing in the range of 300° C. to 400° C.

18. The method of manufacturing a surgical device according to claim 17, wherein annealing step includes annealing for up to 4 hours.

19. The method of manufacturing a surgical device according to claim 14, wherein hardening is performed by forming nanometer-sized ordered zones (mini prisms of 1-3 atom layers) of about 10×0.5 nanometers.

20. The method of manufacturing a surgical device according to claim 14, wherein the hardening includes age hardening in the range of 175° C. to 225° C. for 10 minutes to 3 hours.

21. The method of manufacturing a surgical device according to claim 14, wherein the forming step forms the casting into one of a screw, a plate, a stent, a staple, a wire, and an implant device.

22. The method of manufacturing a surgical device according to claim 14, wherein the forming step forms the casting into one of a clamp, a retractor, forceps or a non-implant device.

23. The method of manufacturing a surgical device according to claim 14, wherein the combined percent of Zn, Ca and Mn in the microalloyed magnesium material in the range of 1.4 to 2.4 percent.

24. A method of fixating bone or tissue of a patient comprising the steps of:
   implanting a fixation device in a patient's body whereby the fixation device secures bone or tissue of the patient together, the fixation device being formed of magnesium (Mg) microalloyed with zinc (Zn), calcium (Ca) and manganese (Mn) to form a microalloyed magnesium material, the microalloyed magnesium material consisting essentially of 0.85 to 1.4 percent by weight of zinc (Zn), 0.2 to 0.5 percent by weight of calcium (Ca), 0.2 to 0.5 percent by weight of manganese (Mn) with the remainder being magnesium (Mg); and
   absorbing the fixation device in the patient's body over time as the bone or tissue heals; and
   continuing to absorb the fixation device in the patient's body over time until the fixation device has been completely absorbed into the body of the patient, whereby surgical removal of the fixation device is not performed on the patient.

25. The method of fixating bone or tissue of a patient according to claim 22, wherein the absorbing of the fixation device in the patient's body over time corresponds to a healing time for the bone or tissue secured by the fixation device.

26. The method of fixating bone or tissue of a patient according to claim 22, wherein the combined percent of Zn, Ca and Mn in the microalloyed magnesium material is varied in the range of 1.5 to 2.4 percent to correspond the absorbing of the fixation device in the patient's body over time to a healing time for the bone or tissue secured by the fixation device.

27. The method of fixating bone or tissue of a patient according to claim 22, wherein the fixation device is one of a screw, plate, sheet, wire or stent.

* * * * *